US010839707B2

(12) United States Patent
Javanbakht

(10) Patent No.: US 10,839,707 B2
(45) Date of Patent: Nov. 17, 2020

(54) AUGMENTED REALITY SYSTEM AND METHOD FOR EXPOSURE THERAPY AND MOTOR SKILLS TRAINING

(71) Applicant: Wayne State University, Detroit, MI (US)

(72) Inventor: Arash Javanbakht, Ypsilanti, MI (US)

(73) Assignee: Wayne State University, Detroit, MI (US)

( * ) Notice: Subject to any disclaimer, the term of this patent is extended or adjusted under 35 U.S.C. 154(b) by 680 days.

(21) Appl. No.: 15/259,844

(22) Filed: Sep. 8, 2016

(65) Prior Publication Data

US 2018/0068577 A1  Mar. 8, 2018

(51) Int. Cl.
*G09B 5/14* (2006.01)
*G06F 3/01* (2006.01)
(Continued)

(52) U.S. Cl.
CPC ............ *G09B 5/14* (2013.01); *G06F 3/011* (2013.01); *G06F 3/012* (2013.01); *G06F 3/015* (2013.01); *G06F 3/016* (2013.01); *G06T 11/60* (2013.01); *G09B 19/003* (2013.01); *G16H 20/70* (2018.01); *G16H 40/67* (2018.01); *H04N 7/147* (2013.01); *H04N 7/152* (2013.01); *G09B 5/02* (2013.01); *G09B 5/065* (2013.01)

(58) Field of Classification Search
CPC .. G09B 5/14; G09B 5/02; G09B 5/065; G06F 3/011; G06F 3/015; G06F 3/0482
USPC ........................................................ 434/236
See application file for complete search history.

(56) References Cited

U.S. PATENT DOCUMENTS 8,758,021 B2 * 6/2014 Takahashi .............. G06Q 10/10
434/262
2011/0213197 A1 * 9/2011 Robertson .............. G16H 50/50
600/27
(Continued)

FOREIGN PATENT DOCUMENTS

WO WO 2015/121253 A1  8/2015

OTHER PUBLICATIONS

Cristina Botella et al, Treating Cockroach Phobia With Augmented Reality, Behavior Therapy, Mar. 20, 2010, pp. 401-413, vol. 41 (2010), published by Elsevier Inc.
(Continued)

*Primary Examiner* — David L Lewis
*Assistant Examiner* — Shauna-Kay Hall
(74) *Attorney, Agent, or Firm* — Fishman Stewart PLLC

(57) ABSTRACT

An exemplary system may include an augmented reality device with a user interface, a processor and memory having a program communicatively connected to the processor. A transceiver may be communicatively connected to a practitioner device for real-time practitioner guidance. The system may include a plurality of sensors and a feedback device in communication with the processor. The system may display initial and updated guidance objects in a real-time environment of the user and in response to sensor outputs of the plurality of sensors. The feedback device may provide at least one of audio, visual, and tactile feedback in response to the sensors outputs. The system may condition the user to provide a desired reaction by guiding the real-time user reactions in the real-time environment using the feedback in response to the sensor outputs.

20 Claims, 5 Drawing Sheets

(51) Int. Cl.
G06T 11/60 (2006.01)
H04N 7/15 (2006.01)
H04N 7/14 (2006.01)
G09B 19/00 (2006.01)
G16H 40/67 (2018.01)
G16H 20/70 (2018.01)
G09B 5/02 (2006.01)
G09B 5/06 (2006.01)

(56) References Cited

U.S. PATENT DOCUMENTS

| | | | | |
|---|---|---|---|---|
| 2012/0302289 | A1* | 11/2012 | Kang | G06F 3/013 455/557 |
| 2014/0019149 | A1* | 1/2014 | Yu | G16H 80/00 705/2 |
| 2014/0204190 | A1* | 7/2014 | Rosenblatt, III | G09B 5/00 348/77 |
| 2014/0266983 | A1* | 9/2014 | Christensen | G02B 27/017 345/8 |
| 2015/0087257 | A1* | 3/2015 | Balram | G06F 3/011 455/404.1 |
| 2015/0170546 | A1* | 6/2015 | Kirenko | G06K 9/00375 434/265 |
| 2016/0246931 | A1* | 8/2016 | Rajan | G06F 19/345 |
| 2017/0323062 | A1* | 11/2017 | Djajadiningrat | G06F 19/324 |

OTHER PUBLICATIONS

Cristina Botella et al, In Vivo versus Augmented Reality Exposure in the Treatment of Small Animal Phobia: A Randomized Controlled Trial, PLOS ONE, Feb. 17, 2016, pp. 1-22.
Mark E. Bouton, Context, Ambiguity, and Unlearning: Sources of Relapse after Behavioral Extinction, Biological Psychiatry, Nov. 15, 2002, pp. 976-986, vol. 52 Issue 10.
Rebekah Bradley et al, A Multidimensional Meta-Analysis of Psychotherapy for PTSD, American Journal of Psychiatry, Feb. 2005, pp. 214-227, vol. 162 Issue 2.
Maria Anne Briscione et al, Conditioned fear associated phenotypes as robust, translational indices of trauma-, stressor-, and anxiety-related behaviors, Frontiers in Psychiatry, Jul. 21, 2014, pp. 1-9, vol. 5 Article 88.
Joann Difede et al, Virtual Reality Exposure Therapy for the Treatment of Posttraumatic Stress Disorder Following Sep. 11, 2001, Journal of Clinical Psychiatry, Nov. 2007, pp. 1639-1647, vol. 68 No. 11.
Elizabeth R. Duval et al, Neural circuits in anxiety and stress disorders: a focused review, Therapeutics and Clinical Risk Management, Jan. 23, 2015, pp. 115-126, vol. 11, published by Dove Medical Press Limited.
Pedro Gamito et al, Virtual Reality Therapy Controlled Study for War Veterans with PTSD. Preliminary Results, Annual Review of Cybertherapy and Telemedicine 2009, Jun. 11, 2009, pp. 269-272, vol. 144, published by IOS Press.
Pedro Gamito et al, PTSD Elderly War Veterans: A Clinical Controlled Pilot Study, Cyberpsychology, Behavior, and Social Networking, Feb. 1, 2010, pp. 43-48, vol. 13 Issue 1, published by Mary Ann Liebert, Inc.
Sarah N. Garfinkel et al, Impaired Contextual Modulation of Memories in PTSD: An fMRI and Psychophysiological Study of Extinction Retention and Fear Renewal, The Journal of Neuroscience, Oct. 1, 2014, pp. 13435-13443, vol. 34 Issue 40.
Maryrose Gerardi et al, Virtual Reality Exposure Therapy Using a Virtual Iraq: Case Report, National Institutes of Health Public Access, 2008, pp. 1-9.
Antonia N. Kaczkurkin et al, Cognitive-behavioral therapy for anxiety disorders: an update on the empirical evidence, Dialogues in Clinical Neuroscience, 2015, pp. 337-346, vol. 17 Issue 3.
Gary B. Kaplan et al, Treatment of addiction and anxiety using extinction approaches: Neural mechanisms and their treatment implications, Pharmacology, Biochemistry and Behavior, Aug. 17, 2010, pp. 619-625, vol. 97 (2011), published by Elsevier Inc.
Richard D. Lane et al, Memory reconsolidation, emotional arousal, and the process of change in psychotherapy: New insights from brain science, Behavioral and Brain Sciences, Jan. 2015, pp. 1-64, vol. 38, published by Cambridge University Press.
Dora Lopresto et al, Neural circuits and mechanisms involved in fear generalization: Implications for the pathophysiology and treatment of posttraumatic stress disorder, Neuroscience and Biobehavioral Reviews, Oct. 28, 2015, pp. 31-42, vol. 60 (2016), published by Elsevier Ltd.
Stephen Maren et al, The contextual brain: implications for fear conditioning, extinction and psychopathology, Nature Reviews Neuroscience, May 2, 2013, pp. 417-428, vol. 14, published by Macmillan Publishers Limited.
Robert N. McLay et al, Exposure Therapy with and without Virtual Reality to Treat PTSD while in the Combat Theater: A Parallel Case Series, Cyberpsychology Behavior and Social Networking, Feb. 11, 2010, pp. 37-42, vol. 13 Issue 1.
Robert N. McLay et al, A Randomized Controlled Trial of Virtual Reality-Graded Exposure Therapy for Post-Traumatic Stress Disorder in Active Duty Service Members with Combat-Related Post-Traumatic Stress Disorder, Cyberpsychology Behavior and Social Networking, Apr. 12, 2011, pp. 223-229, vol. 14 Issue 4.
Robert N. McLay et al, Development and Testing of Virtual Reality Exposure Therapy for Post-Traumatic Stress Disorder in Active Duty Service Members Who Served in Iraq and Afghanistan, Military Medicine, Jun. 2012, pp. 635-642, vol. 177.
Barmen P. McLean et al, Prolonged exposure therapy for post-traumatic stress disorder: a review of evidence and dissemination, Expert Review of Neurotherapeutics, 2011, pp. 1151-1163, vol. 11 Issue 8.
Sarah D. Miyahira et al, The Effectiveness of VR Exposure Therapy for PTSD in Returning Warfighters, Annual Review of Cybertherapy and Telemedicine 2012, 2012, pp. 128-132, published by IOS Press.
Nexhmedin Morina et al, Social interactions in virtual reality exposure therapy: A proof-of-concept pilot study, Technology and Health Care, May 15, 2015, pp. 581-589, vol. 23, published by IOS Press.
Albert Rizzo et al, Development and early evaluation of the Virtual Iraq/Afghanistan exposure therapy system for combat-related PTSD, Annals of the New York Academy of Sciences, Oct. 18, 2010, pp. 114-125, vol. 1208 Issue: Psychiatric and Neurologic Aspects of War.
Maja Wrzesien et al, Analysis of Distributed-Collaborative Activity during Augmented Reality Exposure Therapy for Cockroach Phobia, Annual Review of Cybertherapy and Telemedicine 2010, 2010, pp. 134-139, published by IOS Press.
Maja Wrzesien et al, The Therapeutic Lamp: Treating Small-Animal Phobias, IEEE Computer Graphics and Applications, Feb. 2013, pp. 80-86, vol. 33 Issue 1, published by IEEE Computer Society.
Cristina Botella, Using Augmented Reality to Treat Phobias; 0272-1716/05/2005.
Irene Alice Chicchi Giglioli et al; Augmented Reality: A Brand New Challenge for the Assessment and Treatment of Psychological Disorders; vol. 2015, Article ID 862942, 12 Pages.
Christopher Mims; Treating Cockroach Phobia With Augmented Reality; Jul. 2, 2010; 419653.

* cited by examiner

AUGMENTED REALITY SYSTEM AND METHOD FOR EXPOSURE THERAPY AND MOTOR SKILLS TRAINING

FIELD OF TECHNOLOGY

Exemplary fields of technology for the present disclosure may relate to, for example, augmented reality systems and associated methods for user conditioning.

BACKGROUND

Anxiety and stress-related disorders are common and disabling for individuals, and costly to society. One in three people experience some form of anxiety disorder during their lifetime. Evidence-based treatments for anxiety disorders and Posttraumatic Stress Disorder (PTSD) include antidepressant medications and psychotherapy. Exposure therapy is a treatment for cue-related anxiety disorders such as specific phobias, social phobia, Obsessive Compulsive Disorder (OCD), and PTSD. This includes exposure to feared objects or situations guided by a clinician. For example, in arachnophobia, the fear of spiders, a patient may be exposed to pictures of spiders, and gradually, with help of the clinician, the patient tolerates viewing and approaching the spider. Guidance from the clinician is important for exposure therapy.

Traditional exposure therapy may include exposing a patient to a cue or trigger that initiates fear in the patient while being guided through the fear by the clinician. The patient may learn that a particular trigger is safe, referred to as safety learning, by being exposed to the particular trigger over time and receiving positive feedback from such exposures. Safety learning, however, is context-dependent in that the patient associates safety with a particular environment. Exposure to a multitude of actual environments increases the effectiveness of exposure therapy, although traditional therapies are typically limited to taking place in the office of the therapist, which is not comparable to an actual environment in which fear is likely occur. If the fear is not likely to be reproduced in a clinician's office such as with emotional trauma, traditional therapies may utilize trauma narratives in which the patient repeatedly discusses memories or views images associated with the trauma until the patient feels less anxiety, which also may lack an actual environment that facilitates therapy. Further, virtual reality therapy an entirely computer-generated, virtual environment may be limited by the number of virtual environments and the lack of association by patient between virtual, cartoon-like environments and actual environments, which may result in ineffective association of safety when the exposure to feared objects or situations occurs again in an actual environment. Further, in conditions like combat PTSD, virtual reality therapies provide exposure to the war trauma, not situations in which the PTSD is more likely to be experienced by a veteran such as social interactions, crowded places, and loud noises in the actual environment of the veteran. Traditional techniques thus may have limited environments that do not effectively translate and generalize to the actual environments of the patient, thereby resulting in impaired effectiveness of typical treatments. Accordingly, there is a need for systems and methods that address the shortcomings of traditional exposure therapies.

DETAILED DESCRIPTION

Figure 1:
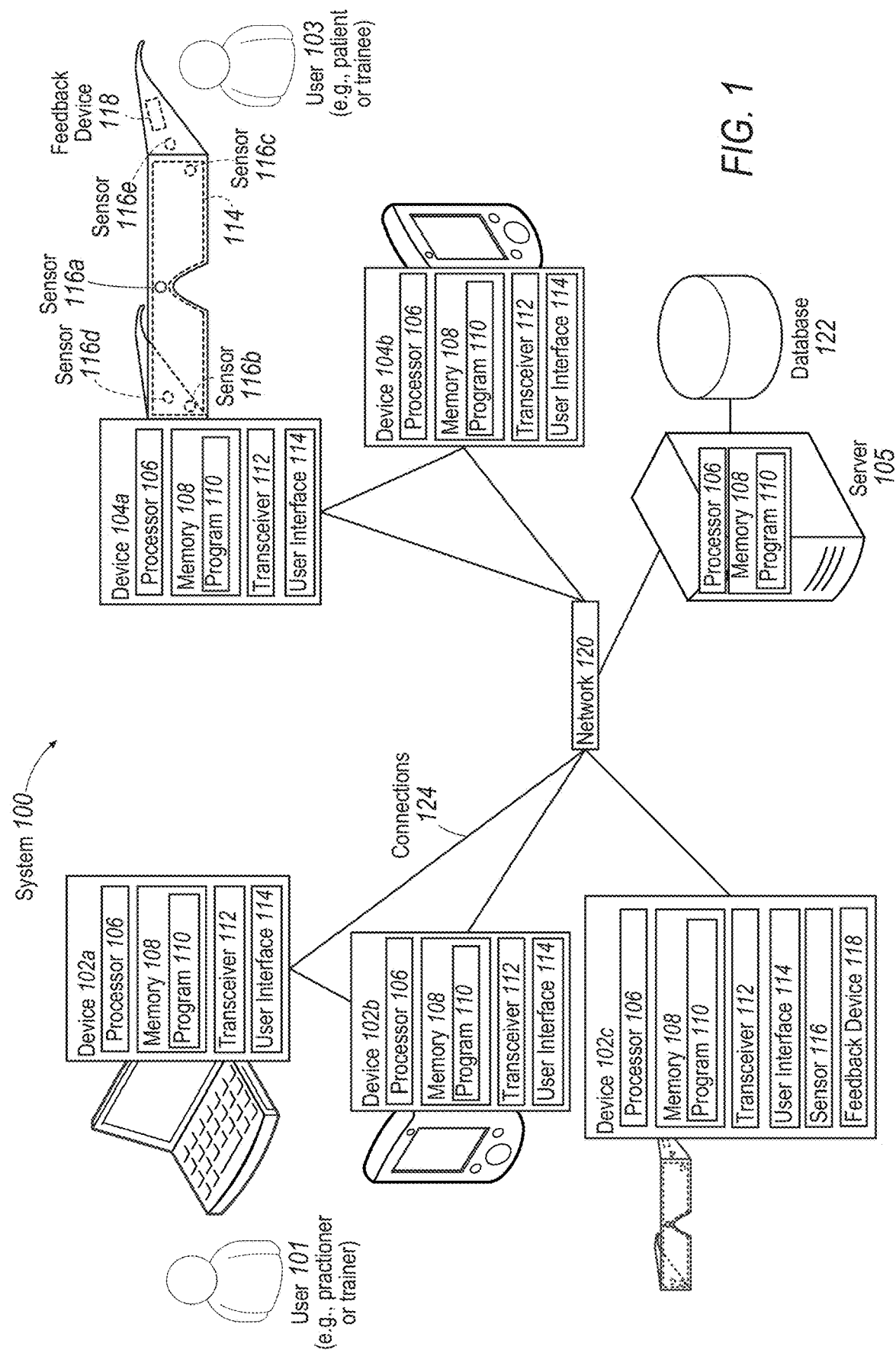
FIG. 1 illustrates an exemplary system of the present disclosure.

An exemplary system may include an augmented reality system that provides exposure therapy with guidance objects that are augmented into or projected on actual environments in real-time and that are specific to a particular patient. The disclosed system may expedite exposure of the patient to a variety of guidance objects (e.g., a cue or trigger that the patient associates with fear) while the patient is in a real-time augmented environment, thereby optimizing the effectiveness of therapy. In addition, such a system may utilize a telepsychiatry connection in which the patient is remotely guided by way of a videoconference, allowing clinician guidance in any real-time environment of the patient. As such, the disclosed systems and methods provide exposure therapy using patient-specific guidance objects in a multitude of real-time augmented environments of the user, thereby conditioning and enhancing generalization of safety learning by the patient and thus improving the efficacy of treatment.

Exemplary systems and methods of the present disclosure may utilize augmented reality to provide context-specific therapy while the patient is experiencing a real-time augmented environment. A system and method may be suitable for exposure therapy and motor skills training. This may include, for example, conditioning a user to provide a desired reaction, for example, in response to a cue or trigger feared by the patient. The system may be configured to display an augmented reality image of a guidance object such as a cue or trigger, provide a sound or tactile output providing a sensation to the user associated with the cue or trigger, or generate any other sensory output associated with the cue or trigger. The system may be configured to generate combination guidance objects, e.g., combining an augmented reality image and sound or vibration associated with the guidance object. The augmented reality image displayed in an augmented portion of a user interface that also has a transparent portion so that the augmented reality image appears over a real-time environment of a user.

As another example, the augmented reality image may include a holographic image. The holographic image may be projected from a projector device (e.g., a three-dimensional holographic or hologram projector) as part of or in communication with the devices of the users. The projector device may project the holographic image onto the real-time environment of the user. For example, the projector device may project a holographic image of spider onto the real-time environment such as a home of a patient.

Alternatively or in addition, the system may be configured to generate augmented environments. Augmented environments may be displayed by way of a user interface or projected by way of a projector device. The system may be configured to generate one or more guidance objects that include an augmented cue or trigger and an augmented environment that is superimposed over or projected on an actual, real-time environment. For example, guidance objects may include an image of cue or trigger (e.g., a war zone) displayed over or projected onto a real-time environment of the user (e.g., a shopping mall) along with vibration and sounds associated with the cue or trigger (e.g., gunfire and explosions) in the real-time environment.

The guidance object may include any visual, audible, or tactile output or a combination thereof. The guidance object may be any output that initiates a reaction from a user (e.g., fear or safety) or guides a mental or physical reaction of the user (e.g., a superimposed or overlaid limb that encourages the user to follow its movement). A guidance object may include any visual (e.g., image), auditory (sound or speech), or haptic (e.g., tactile such as vibration) output or combination thereof. For example, the guidance object may include or be associated with a spider, an explosion, an earthquake, music, or a musical instrument such as playing a piano. As another example, the system may generate a combination guidance object such as music accompanying an augmented reality image of fingers of a music instructor playing the music over the real-time environment that includes the piano and the fingers of the user, which may guide the user toward a desired reaction of playing the music according to the movements of the music instructor. Guidance objects may include any animate or inanimate objects, human-like avatars, sounds, or anything that may guide a user toward a desired reaction, such as feeling a sense of safety in an environment that may otherwise cause fear in the user.

An exemplary system may be utilized to treat any type of physical, mental, or psychological disorder or encourage any type of physical or mental reaction or learning in response to guidance objects. A system may be configured to treat, for example, post-traumatic stress disorder, obsessive compulsive disorder, any anxiety disorder, drug additions, specific phobias, social phobia, emotional trauma, behavioral additions, and fears associated with animals, flight, height, or any other object or situation. A system may further be utilized for any type of learning such as for learning to play sports or musical instruments. A system may further utilize guidance objects including augmented reality images of people, avatars, sounds, environments, or cue or trigger reminder. In addition, a system may be utilized to enhance physical training or rehabilitation to improve brain, nerve, or muscle responses, e.g., due to brain or body injury.

The system may include an augmented reality device with a user interface, a processor, and memory having a program communicatively connected to the processor. A transceiver may be communicatively connected to a local or remote practitioner device for real-time guidance from a practitioner. Alternatively or in addition, the system may include a plurality of sensors and a feedback device in communication with the processor. The system may display or present one or more guidance objects such as initial and updated guidance objects in response to the practitioner device or sensor outputs of the plurality of sensors. The feedback device may provide at least one of audio, visual, and tactile feedback in response to practitioner device or the sensors. The guidance objects may be associated with a treatment plan for a desired reaction of the user. For example, the initial guidance object may include a cue associated with a trigger feared by the patient, exposure to which may produce a desired reaction of safety learning as observed by the practitioner or indicated by the sensors longer providing sensor outputs associated with fear. The updated guidance object may include a similar or alternative cue so as to expand the safety learning by the user. The initial and updated guidance objects may include visual, auditory, and tactile outputs or a combination thereof. By providing updated guidance objects, the system may condition the user to provide a desired reaction by guiding the real-time user reactions.

The system may be configured to provide at least one of initial guidance objects and updated guidance objects in response to sensor outputs of one or more sensors and provide visual, audio, and tactile feedback by a feedback device. For example, the system may provide operations including to display by way of the user interface an initial guidance object associated with the treatment plan for a desired reaction of the user, receiving a first sensor output of the sensor indicating a first reaction of the user to the initial guidance object, comparing the first reaction and the desired reaction, generating an updated guidance object in response to the comparison of the first reaction and the desired reaction, and displaying the updated guidance object based on the comparison of the first reaction and the desired reaction. Further, the system may initiate at least one of a video, audio, and tactile connection with a local or remote practitioner device. The present disclosure also includes corresponding methods and instructions, or operations of a non-transitory computer-readable medium with a program executed by a computing device with a hardware processor. The exemplary system may perform any or all of the operations automatically (e.g., based on sensor outputs), in response to user inputs (e.g., of the practitioner or patient), or a combination thereof. Accordingly, the exemplary system may expedite exposure of the user to a variety of cues and real-time environments, thereby optimizing the effectiveness of therapy.

FIG. 1 illustrates an exemplary system 100, for example, to generate and communicate guidance information such as user guidance information including, for example, initial and updated guidance objects, first and second sensor inputs or measurements, first and second sensor outputs, and audio, video, and tactile feedback. System 100 may take many different forms and include multiple and/or alternate hardware components and facilities. While an exemplary system 100 is shown in FIG. 1, the exemplary components illustrated in FIG. 1 are not intended to be limiting, may be optional, and are not essential to any other component or portion of system 100. Indeed, additional or alternative components and/or implementations may be used.

System 100 may include or be configured to be utilized by user 101 such as a practitioner, trainer, or instructor and user 103 such as a patient, trainee, or student. System 100 may include one or more of devices 102a, 102b, 102c, devices 104a, 104b, server 105, processor 106, memory 108, program 110, transceiver 112, user interface 114, sensors 116a, 116b, 116c, 116d, 116e, feedback device 118, network 120, database 122, and connections 124. Device 102 may include any or all of device 102a (e.g., a desktop, laptop, or tablet computer), device 102b (e.g., a mobile or cellular phone), and device 102c (e.g., an augmented reality device such as augmented reality glasses). Device 104 may include any or all of device 104a (e.g., an augmented reality device) and device 104b (e.g., a mobile or cellular device). Processor 106 may include a hardware processor that executes program 110 to provide any or all of the operations described herein (e.g., by device 102, device 104, server 105, database 122, or any combination thereof) and that are stored as instructions on memory 108 (e.g., of device 102, device 104, server 105, or any combination thereof.

An exemplary system 100 may include user interface 114, processor 106, and memory 108 having program 110 communicatively connected to the processor 106. The system 100 may further include transceiver 112 that may be communicatively connected to one or a plurality of sensors 116 associated with a user, e.g., as part of device 102, 104, or a combination thereof. The system 100 using the processor 106 may provide operations that include displaying by way of the user interface 114 an initial guidance object associated with a treatment plan for a desired reaction (e.g., at least one of a reduced reaction and an increased reaction, mental or physical, to a guidance object such as a cue or a trigger) of the user 103 that is defined by user 101 by way of user interface 114, receiving by way of the transceiver 112 a first sensor output of the sensor 116 indicating a first reaction of the user 103 to the initial guidance object, comparing by way of the processor 106 the first reaction and the desired reaction of the user 103, generating by way of the processor 106 an updated guidance object in response to the comparison of the first reaction and the desired reaction of the user 103, and displaying by way of the user interface 106 the updated guidance object based on the comparison of the first reaction and the desired reaction. The system 100 may be configured to generate guidance objects that include audible and tactile outputs associated with the cue or trigger, e.g., the sounds of a spider for arachnophobia treatment or the sounds and vibration of gunfire for PTSD treatment. Further, the processor 106 may initiate at least one of a video, audio, and tactile connection with a local or remote practitioner device, e.g. in person or remotely. The system 100 may perform any or all of the operations automatically in response to sensor outputs or in response to user inputs of the user 101 or 103, e.g., user 101 being a practitioner, trainer, or instructor and user 103 being a patient, trainee, or student. In addition, such operations may be implemented by way of corresponding methods of a computing device or instructions of a non-transitory computer-readable medium. Accordingly, the exemplary system 100 may expedite exposure of the user 103 to a variety of cues and real-time environments with the guidance of user 101, thereby optimizing the effectiveness of system 100.

Furthermore, the system 100 using the processor 106 may provide operations including receiving by way of the transceiver 112 a second sensor output of the sensor 116 indicating a second reaction of the user 103 in response to the updated guidance object, comparing by way of the processor 106 the second reaction, the first reaction, and the desired reaction, generating by way of the processor 106 a further updated guidance object in response to the comparison of the second reaction, the first reaction, and the desired reaction, and displaying by way of the user interface 114 the updated guidance object based on the comparison of the second reaction, the first reaction, and the desired reaction. The system 100 using processor 106 may provide operations including providing by way of a feedback device 118 in communication with the processor 106 at least one of audio, visual, and tactile feedback in response to at least one of the first and second sensor outputs to facilitate the desired reaction.

The system 100 may include an overall network infrastructure through which any of devices 102 and 104, server 105, and database 122 may communicate, for example, to transfer information between any portion of system 100 using connections 124. In general, a network (e.g., system 100 or network 120) may be a collection of computing devices and other hardware to provide connections and carry communications. The devices 102 and 104 may include any computing device such as include a mobile device, cellular phone, smartphone, smartwatch, activity tracker, tablet computer, next generation portable device, handheld computer, notebook, laptop, projector device (e.g., three-dimensional holographic or hologram projector), or virtual reality or augmented reality device. Devices 102 and 104 may include processor 106 that executes program 110. Device 102 may include memory 108 that stores guidance information and program 110. The device 102 may include transceiver 112 that communicates guidance information between any of devices 102 and 104, sensors 116, feedback device 118, server 105, and database 122.

The server 105 may include any computing system. Server 105 may generate by processor 106 executing program 110 and store by memory 106, e.g., guidance information such as guidance objects related to users 101 and 103 and devices 102 and 104. Server 105 may further generate and store guidance information including a user profile for users 101 and 103. Server 105 may be configured to generate and store guidance information including a medical history of users 103. The server 105 may communicatively connect with and transfer information with respect to devices 102, devices 104, sensors 116, feedback device 118, and database 122. Server 105 may be in continuous or periodic communication with devices 102, devices 104, sensors 116, feedback device 118, and database 122. Server 105 may include a local, remote, or cloud-based server or a combination thereof and may be in communication with and provide guidance information (e.g., as part of memory 108 or database 122) to any or a combination of devices 102 and 104. The server 105 may further provide a web-based user interface (e.g., an internet portal) to be displayed by user interface 114. The server 105 may communicate the guidance information with devices 102 and 104 using a notification including, for example automated phone call, short message service (SMS) or text message, e-mail, http link, web-based portal, or any other type of electronic communication. In addition, the server 105 may be configured to store guidance information as part of memory 108 or database 122. The server 105 may include a single or a plurality of centrally or geographically distributed server 105. Server 105 may be configured to store and coordinate guidance information with and between any of devices 102, devices 104, and database 122.

Device 102*c* and 104*a* may include an augmented reality device such as any device configured to provide a computer-simulated, augmented reality output, e.g., visual, auditory, haptic (e.g., tactile), or a combination thereof, within or over a portion of an environment that is being experienced in real-time by a user such as user 103. Devices 102*c* and 104*a* may be powered or operatively connected to another computing device or may be battery powered. Devices 102*c* and 104 may include a head mounted (e.g., augmented reality glasses), hand held device (e.g., a mobile or cellular phone), projector device (e.g., three-dimensional holographic or hologram projector), or a desktop, laptop, or tablet device configured to display a guidance object. Device 102*c* and 104*a* may include an augmented reality device configured to display in real-time, by way of user interface 114, a transparent area and an augmented area. The transparent area may allow the user to view a real-time environment of the user 101 or 103. The augmented area may display an augmented reality image over the real-time environment. The augmented reality image may include at least one of the initial and updated guidance objections in response to execution of the program 110 by processor 106.

System 100, or any portion of system 100 such as devices 102*c* and 104*a*, may include one or more sensors 116 configured to receive sensor inputs and provide sensor outputs, e.g., including guidance information associated with a user reaction of user 101 or 103. Sensor 116 may include any wired or wireless sensor attached to or otherwise associated with user 101 or 103. Exemplary sensors 116 may be part of device 102c or 104a such as an augmented reality device (e.g., augmented reality glasses) and may include sensor 116a including a forward-facing sensor providing a field of view of user 101 or 103, sensor 116b including a user-facing sensor toward a first or right eye of user 101 or 103, sensor 116c including a user-facing sensor toward a second or left eye of user 101 or 103, sensor 116d may include a user-facing sensor toward a first or right temple of user 101 or 103, and sensor 116e may include a user-facing sensor toward a second or left temple of user 101 or 103.

Sensor 116 may include, for example, any health monitor or any wearable, contact, or non-contact sensor. The sensor 116 may be unattached, releasably attached, or permanently attached with respect to the user, devices 102c or 104a, or accessories of the user (e.g., clothing, shoes, glasses, or jewelry). Sensor 116 may be configured to receive inputs associated with users 101 and 103 and generate sensor outputs related to any biological, bodily, or environmental parameter related to user 101 or 104, and such sensor outputs may be displayed to users 101 and 103 by way of user interface 114. An exemplary sensor 116 may include any sensor configured to measure bodily parameters including, for example, heart rate, heart rate variability, pupil dilation, galvanic skin responses (e.g., skin conductance responses), or electroencephalography, glucose level, respiratory rate, eye response, oxygen saturation, blood pressure, body temperature, or a combination thereof. An exemplary sensor 116 may further include a muscle contraction sensor, a heart rate monitor, cardiac sensor, blood glucose meter, respirometer, spirometer, respiration sensor, optical sensor, electrocardiogram (EKG), medical imaging device, medical radar device, pulse oximeter, blood pressure monitor, body temperature monitor, breathalyzer, chemical sensor, or moisture sensor. Sensor 116 may include also a microphone, camera, scanner, earbud, etc., or a combination thereof. Sensors 116 may be communicatively connected to or part of devices 102 and 104, e.g., devices 102c and 104a. The sensors 116, using transceiver 112, may be configured to communicate sensor outputs (e.g., real-time, near real-time, periodically, or upon request of user 101 or 103) to any or all of devices 102 and 104, server 105, and database 122.

The sensor outputs of sensors 116 may indicate user reactions (e.g., anxiety, arousal, craving, or any other human reaction), environmental and other parameters, and combinations thereof. In response to sensor outputs of sensors 116, the system 100 may provide at least one of audio, visual, or tactile feedback to or between users 101 and 103. The sensor outputs of sensors 116 may be included as part of the guidance information, which may be utilized for research, clinical observation, or biofeedback purposes. In use, the devices 102 and 104 may receive (e.g., using the user interface 114) guidance information from the users 101 and 103, receive (e.g., using transceiver 112 by way of network 120) guidance information from one or more of sensors 116 and server 105, display (e.g., with user interface 114) guidance information, communicate (e.g., using the transceiver 112 by way of network 120) the guidance information to any of devices 102 and 104, server 105, and database 122, and cause storage of guidance information on memory 108 or database 122.

The user interface 114 of devices 102 and 104 may include any user interface device, display device, or other hardware mechanism that connects to a display or supports user interfaces so as to communicate and present guidance information throughout the system 100. Any of the inputs into and outputs from user interface 114 may be included into guidance information. The user interface 114 may include any input or output device to facilitate receipt or presentation of information (e.g., guidance information) in audio, visual or tactile form or a combination thereof. Examples of a display may include, without limitation, a touchscreen, cathode ray tube display, light-emitting diode display, electroluminescent display, electronic paper, plasma display panel, liquid crystal display, high-performance addressing display, thin-film transistor display, organic light-emitting diode display, surface-conduction electron-emitter display, laser TV, carbon nanotubes, quantum dot display, interferometric modulator display, projector device, and the like. The user interface 114 may present guidance information to any user of devices 102 and 104.

The feedback device 118 may be configured to provide audio, visual, and tactile feedback, e.g., sound, visual, and vibration indicators in response to the user reactions. The feedback device 118 may include a speaker, display, or vibration device. Feedback device 118 may be configured to provide feedback for correction of motions. Feedback device 118 may be part of device 104a, e.g., an augmented reality device. Feedback device 118 may also include wearable sleeves or devices that will give any form of tactile signal (e.g. vibration) to the user 103 (e.g., limbs or extremities). Feedback device 118 may be configured to inform user 103 to increase or decrease movement or force in a particular direction. For instance, if the user 103 is overextending a limb (e.g., an arm), feedback device 118 will apply tactile feedback (e.g., a vibration) to the outside of the limb, informing user 103 of the overextension. Feedback device 118, by way of user interface 114, may provide visual feedback associated with the relative or degree of motion for user 103, e.g., a first or red colored zone displayed on user interface 114 showing an excessive or higher amount of motion, a second or green colored zone showing sufficient or moderate amount of motion, or a third or blue colored zone showing insufficient or lower amount of motion. Feedback device 118, by way of user interface 114, may display the relative or degree of motion on corresponding parts of an anatomic model of a human overlaid on a portion or corner of user interface 114. Feedback device 118 may also be configured to provide auditory feedback, e.g., sound including a noise or a voice indicating motion corrections.

The connections 124 may be any wired or wireless connections between two or more endpoints (e.g., devices or systems), for example, to facilitate transfer of guidance information. Connection 124 may include a local area network, for example, to communicatively connect the devices 102 and 104 with network 120. Connection 124 may include a wide area network connection, for example, to communicatively connect server 105 with network 120. Connection 124 may include a wireless connection, e.g., radiofrequency (RF), near field communication (NFC), Bluetooth communication, Wi-Fi, or a wired connection, for example, to communicatively connect the devices 102 and 14, sensors 116, and feedback device 118.

Any portion of system 100, e.g., devices 102 and 104 and server 105, may include a computing system and/or device that includes a processor 106 and a memory 108. Computing systems and/or devices generally include computer-executable instructions, where the instructions may define operations and may be executable by one or more devices such as those listed herein. Computer-executable instructions may be compiled or interpreted from computer programs created using a variety of programming languages and/or technologies, including, without limitation, and either alone or in combination, Java language, C, C++, Visual Basic, Java Script, Perl, SQL, PL/SQL, Shell Scripts, Unity language, etc. The system 100, e.g., devices 102 and 104 and server 105 may take many different forms and include multiple and/or alternate components and facilities, as illustrated in the Figures. While exemplary systems, devices, modules, and sub-modules are shown in the Figures, the exemplary components illustrated in the Figures are not intended to be limiting. Indeed, additional or alternative components and/or implementations may be used, and thus the above communication operation examples should not be construed as limiting.

In general, computing systems and/or devices (e.g., devices 102 and 104 and server 105) may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., the BlackBerry OS distributed by Research In Motion of Waterloo, Canada, and the Android operating system developed by the Open Handset Alliance. Examples of computing systems and/or devices such as devices 102, devices 104, and server 105 may include, without limitation, mobile devices, cellular phones, smart-phones, super-phones, next generation portable devices, mobile printers, handheld or desktop computers, notebooks, laptops, tablets, wearables, virtual or augmented reality devices, secure voice communication equipment, networking hardware, computer workstations, or any other computing system and/or device.

Further, processors such as processor 106 receive instructions from memories such as memory 108 or database 122 and execute the instructions to provide the operations herein, thereby performing one or more processes, including one or more of the processes described herein. Such instructions and other guidance information may be stored and transmitted using a variety of computer-readable mediums (e.g., memory 108 or database 122). Processors such as processor 106 may include any computer hardware or combination of computer hardware that is configured to accomplish the purpose of the devices, systems, operations, and processes described herein. For example, the processor 106 may be any one of, but not limited to single, dual, triple, or quad core processors (on one single chip), graphics processing units, and visual processing hardware.

A memory such as memory 108 or database 122 may include, in general, any computer-readable medium (also referred to as a processor-readable medium) that may include any non-transitory (e.g., tangible) medium that participates in providing guidance information or instructions that may be read by a computer (e.g., by the processors 106 of the devices 102 and 104 and server 105). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including radio waves, metal wire, fiber optics, and the like, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Further, databases, data repositories or other guidance information stores (e.g., memory 108 and database 122) described herein may generally include various kinds of mechanisms for storing, providing, accessing, and retrieving various kinds of guidance information, including a hierarchical database, a set of files in a file system, an application database in a proprietary format, a relational database management system (RDBMS), etc. Each such guidance information store may generally be included within (e.g., memory 108) or external (e.g., database 122) to a computing system and/or device (e.g., devices 102 and 104 and server 105) employing a computer operating system such as one of those mentioned above, and/or accessed via a network (e.g., system 100 or network 120) or connection in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above. Memory 108 and database 122 may be connected to or part of any portion of system 100.

Figure 2:
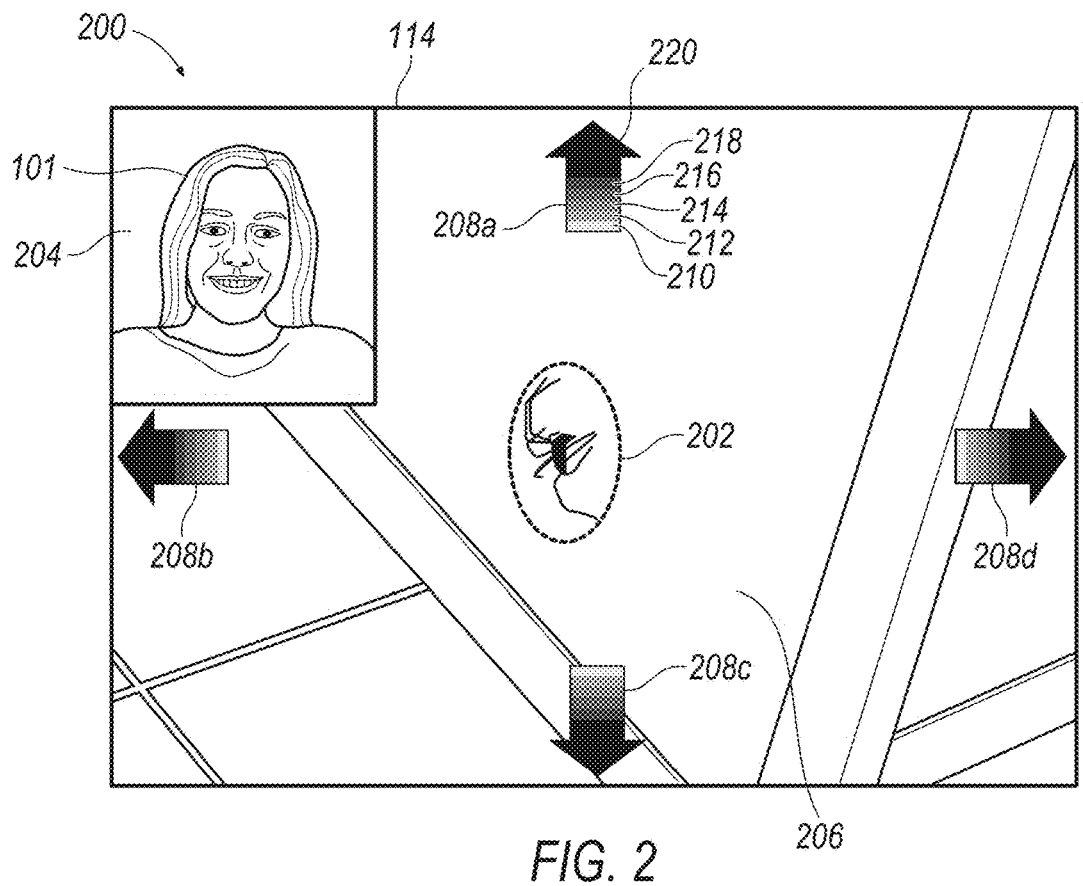
FIG. 2 illustrates an exemplary display screen of the present disclosure.
Figure 3:
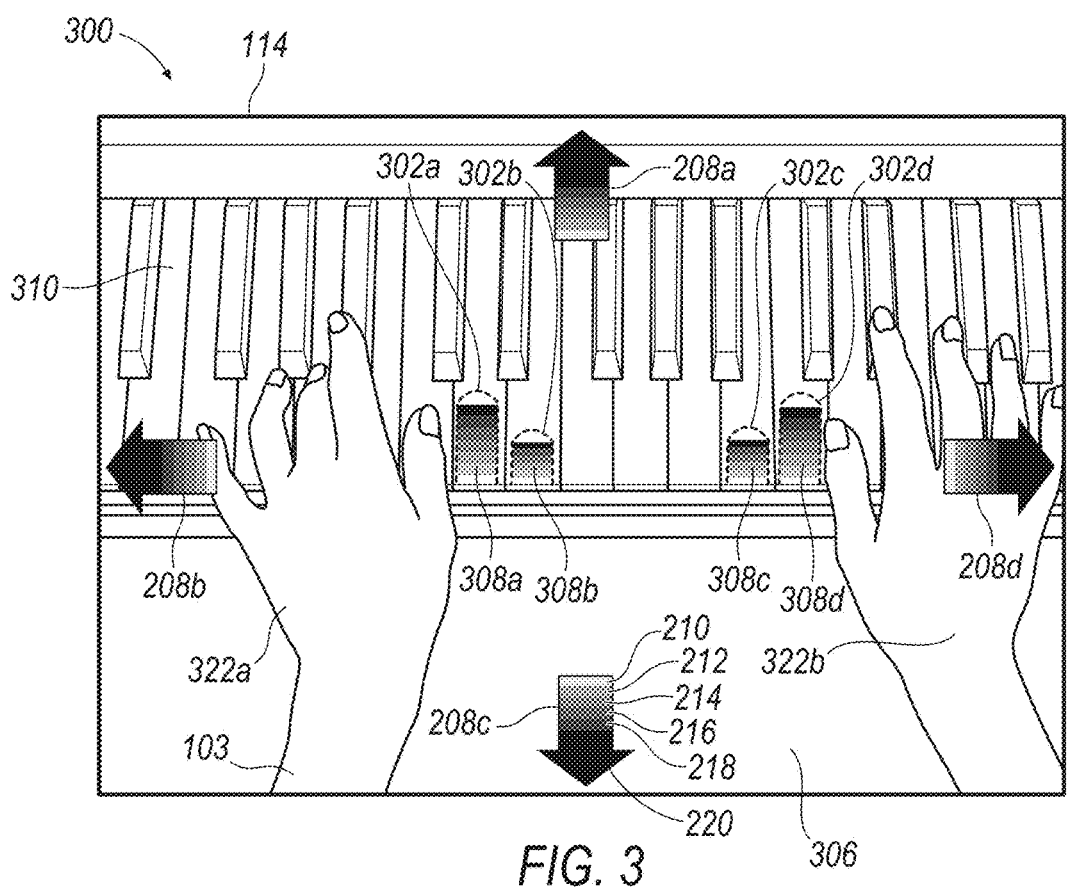
FIG. 3 illustrates another exemplary display screen of a user interface.
Figure 4:
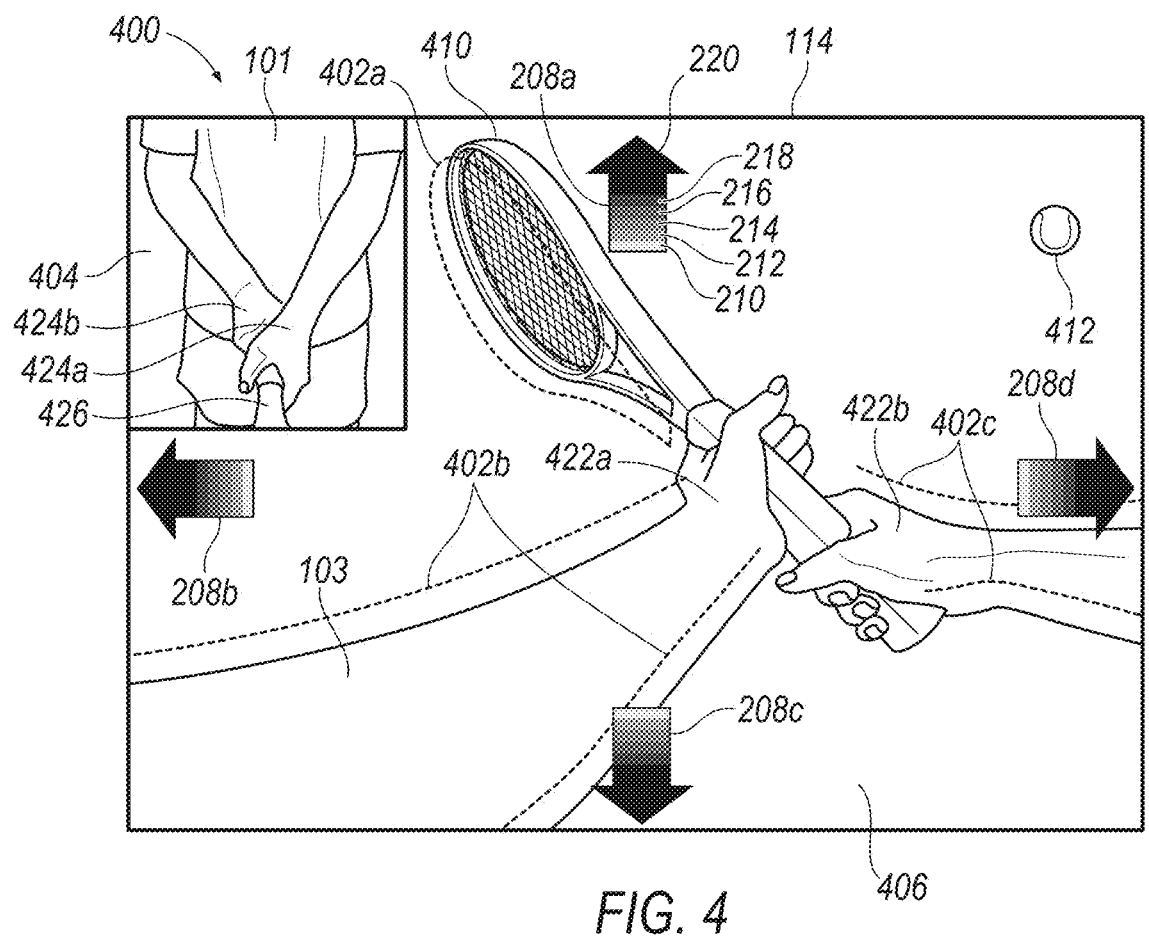
FIG. 4 illustrates another exemplary display screen of a user interface.

FIGS. 2-4 respectively illustrate exemplary display screens 200, 300, and 400 as part of user interface 114, e.g., to receive and display guidance information between users 101 and 103. Examples may take many different forms and include multiple and/or alternate components. While certain examples are respectively shown in the Figures, the exemplary components illustrated are not intended to be limiting, may be optional, and are not essential to any other step or component. Indeed, additional or alternative components and/or implementations may be used.

FIG. 2 illustrates display screen 200 to be displayed on user interface 114, e.g., for receiving inputs and displaying outputs between users 101 and 103, e.g., for treating a physical, mental, or psychological disorder of user 103. User interface 114 may include an augmented portion 202 with an augmented reality image of guidance object as discussed above (e.g., illustrated as a cue or trigger associated with a spider feared by a patient), a guidance window 204 displaying user 101 or 103 (e.g., a practitioner providing guidance to the patient), an environment portion 206 of a real-time environment of the user 101 or 103 (e.g., at a mall, in a car, or at home such as in a living room, bathroom, or bedroom or on a porch), and guidance indicators 208 providing visual guidance in response to user reactions of user 101 or 103 (e.g., urging the patient toward, away, or sideways relative to the guidance object in response to the user reactions of the patient). The guidance window 204 may display at a video connection (e.g., a videoconference) with a practitioner and allow the exchange of guidance information between users 101 and 103. The environment portion 206 may allow the user 103 to view in real-time the real-time environment of the user 103, e.g., the field of view of user 101 by way of sensors 116. The augmented portion 202 may include a spider that is feared by the user 103, allowing the practitioner to receive user reactions of user 103 by the videoconference and sensors 116 and guide the user reactions and safety learning by way the videoconference and guidance indicators 208. User interface 114 may provide the initial guidance object specified by way of the user interface 114 and provide one or more updated guidance objects with an updated speed, distance, direction, or a combination thereof in response to a user reaction of user 103 or inputs from user 101.

Furthermore, user interface 114, by processor 106 executing program 110, may display guidance objects such as a cue or trigger (e.g., a spider) to provide exposure therapy (e.g., to treat a phobia such as spider phobia), in the real-time environment of user 103, and with the guidance object at distance and with a speed and a direction as defined by the user 101 or 103 by way of user interface 114. The guidance object may include visual, auditory, and tactile components comparable to the cue or trigger, e.g., visual appearance of a spider and sounds and vibration associated with movement of the spider. The guidance object may include an avatar with an appearance, voice, and speech content selected or edited by user 101 or 103 using user interface 114.

The user 101 may include any user of device 102 such as any practitioner or trainer and user 103 may include any user of device 104 such as any patient or trainee. A practitioner may include a clinician, a healthcare provider, a physician, a psychiatrist, a psychologist, a psychotherapist, a physical therapist, or social worker. User 101 may be any person that provides guidance, instruction, or training to user 103. User 103 may include any person receiving guidance, instruction, or training. User 101 or 103 by way of user interface 114 may identify one or more guidance objects to be displayed by user interface 114, e.g., for exposure treatment that displays an object, person, or situation which is feared, avoided, or craved by user 103. User interface 114 will display to user 101 what is in the field of view of user 103, e.g., by way of sensors 116. User interface 114 may display to user 103 a guidance object including an augmented reality image of user 101, hear a guidance object including a sound such as the voice of the user 101. Alternatively or in addition, corresponding images and sounds of user 103 may be provided to user 101.

The disclosure may include user 103 positioning, by way of user interface 114, guidance objects such as one or more cue, image (e.g., avatar), sound, or a combination thereof, e.g., an augmented reality image in an augmented portion of user interface 114 that is displayed to user 103 while the user 103 is experiencing his or her real-time environment. User 103 may see and hear, by way of user interface 114, the user 101 including a visual image of user 101 and an audible voice of user 101. User 103, by way of device 102, may place guidance objects in the user interface 114 of device 104. User 103 may further direct the guidance objects including their motion and conversation content displayed on device 104.

User interface 114, by processor executing program 110, may be configured display guidance objects to treat a variety of physical, mental, and psychological disorders. Guidance objects may be configured to anxiety disorders (e.g., generalized anxiety disorder or unspecified anxiety disorder). Further, guidance objects may be associated with phobias such as animals and insects, special situations (e.g., flying, public transportation, bridges, tunnels, closed-in spaces, or crowded spaces), a natural event (e.g., a storm, heights, water, or natural disasters), blood, injection, injuries, characters, clowns, loud noise, etc. Guidance objects may include an audience or crowd so as to treat social phobia or fear of public performance. Guidance objects may further be configured to treat obsessive compulsive disorder or post-traumatic stress disorder in military personnel and civilians. Guidance objects may also be configured to treat drug addictions related to cigarettes, cigars, alcohol, and other drugs. Guidance objects may be associated with any area of substance use related disorders or any form of addiction, e.g., guidance objects may include or be related to cigarettes, alcohol, illicit drugs, prescription drugs, marijuana, nicotine, sex, pornography, shopping, videogames, or the internet. Guidance objects may be associated with impulse control disorders such as kleptomania, gambling, pyromania, trichotillomania. Guidance objects may be associated with eating disorders. Guidance objects may be utilized to treat post-traumatic stress disorder such as people that are easily startled in that any unpredicted loud noise may be a trigger to anxiety, e.g., guidance objects may include people, noise, and any reminder of the trauma. User 101 or 103 may type or select from a library of scripts including words to be spoken by the guidance objects such as avatars for interaction with the user 101 or 103 or the other of user 101 or 103. Guidance objects may also be associated with views from inside or outside a window of a house, suspicious people on a street, kids playing outside, screaming, lightning, or fireworks.

User interface 114, by processor 106 executing program 110, may also display guidance objects such that users 101 and 103 may interactively practice the exposure to the guidance objects. User interface 114 may display the guidance objects in a graded manner or sequence, e.g., in response to a preparation level of user 103 and an expertise level of user 103. Users 101 and 103, by way of user interface 114, may design guidance objects including scenarios that may be utilized at a later time by user 103 without the guidance of user 101. A non-clinical version of this application may be used independent of providers, and offline by public as an application with pre-designed scenarios, or scenarios determined by the users.

Moreover, user interface 114, by processor 106 executing program 110, may display guidance indicators 208 to guide the user 103 in response to user reactions received by way of videoconference, sensors 116, or a combination thereof. The guidance indicators 208 may include guidance indicator 208a (e.g., guiding the user 103 forward or directly toward the augmented reality image in response to the practitioner by the videoconference or the sensors 116 measuring a user reaction indicating a high level of learning for user 103), guidance indicator 208b (e.g., guiding the user 103 to a first or left side relative to the augmented reality image in response to the practitioner by the videoconference or the sensors 116 measuring a user reaction indicating a moderate level of learning for user 103), guidance indicator 208c (e.g., guiding the user 103 to a second or lower direction relative to the augmented reality image in response to the practitioner by the videoconference or the sensors 116 measuring a user reaction indicating a moderate level of learning for user 103), and guidance indicator 208d (e.g., guiding the user 103 to a second or right side relative to the augmented reality image in response to the practitioner by the videoconference or the sensors 116 measuring a user reaction indicating a moderate level of learning for user 103). Guidance indicators 208 may each include a first or minimum levels 210, a second level 212, a third level 214, a fourth level 216, and a fifth level 218, and a sixth or maximum level 220 (e.g., guiding the user 103 with a level of speed, distance, or force for the user 103 to move or apply in response to the practitioner by the videoconference or the sensors 116 measuring a user reaction indicating the corresponding level of learning for user 103.

The user interface 114, by processor 106 executing program 110, may display also guidance objects associated with addictive cues, e.g., to treat drug addiction. Exposure to the desired addictive cues may desensitize the user and help them develop a desired reaction including self-restraint with respect to or control over their desire for the drug. The system may utilize a real-time environment of the patient such a drug use location where the patient usually uses the drug, e.g., the home of the patient. The system may additionally provide exposure while the patient is guided by a practitioner using a telepsychiatry connection.

In another example, user interface 114, by processor 106 executing program 110, may display guidance objects associated with trauma or violence, e.g., to treat veterans or assault victims. For veterans, the system may expose the patient to a trigger associated with fear and flashback responses from war that are experienced in their daily environment, which may prevent them from being able to enjoy daily activities such as going to a mall. Veterans may, for example, have a trigger such as violence that occurred in a war location, e.g., a gunfight in the streets of Iraq. Rather than exposing the patient to a virtual reality, cartoon-like environment associated with the war location for which the patient is unlikely to return, the system may display an augmented reality image of a cue while allowing the user to experience their real-time environment, e.g., visual, audio, and tactile outputs of gunfire or a comparable output such as a car backfiring while allowing the user to view the actual, real-time environment such as a home or an auto show. The guidance object may also include safe cues that resemble some but not all of the features of the cue or trigger that initiates a fear reaction in patient (e.g., with PTSD), e.g., a loud noise, people arguing, lightning, children playing guns, or carrion.

As another example, user interface 114, by processor 106 executing program 110, may display guidance objects such as a practitioner or avatar that is superimposed or overlaid on a real-time environment of the user. For example, user interface 114 may display a telepsychiatry connection between devices 102 (e.g., a local or remote practitioner device) and device 104 (e.g., a patient device) for exposure in the real-time environment while a patient is being guided by a practitioner. User interface 114 may also display a telepsychiatry connection between devices 102 and 104, e.g., bringing an augmented reality image of the practitioner to the real-time environment of the patient to facilitate exposure therapy. For instance, an augmented reality image of user 101 (e.g., the practitioner) may be displayed in user interface 114 of user 103 (e.g., the patient) so as to accompany the patient in a trauma location (e.g., a gas station parking lot in which the patient was previously assaulted) and so that user 101 may guide the user 103 through the fear and facilitate safety learning. As another example, the user interface 114 may display a guidance object including an avatar that looks the same as or similar to someone that the user 103 associates with fear, e.g., someone that previously assaulted the user 103. As such, the user interface 114 may display one or more guidance objects in the real-time environment of user 103 to facilitate a user reaction for user 103 that is associated with a desired reaction such as reduced fear or increased safety.

Guidance information may be received and displayed by user interface 114 and stored in memory 108, database 122, or a combination thereof. Guidance information may include a library or plurality of guidance objects. Guidance objects may include any animate or inanimate object, e.g., insects, animals, or human-like avatars. Guidance objects may include cues or aviators for augmented display in the real-time environment of the user. Guidance information may include a range selection, direction selection, and a speed selection to be displayed by user interface 114 corresponding to the movement of one or more guidance objects. The user interface 114 may be configured to receive typed or spoken words from user 101 or 103 and in response display or speak (e.g., as part of a guidance object such as an avatar) the words to the other of the user 101 or 103.

FIG. 3 illustrates system 300 with user interface 114 configured to display guidance objects, e.g., for receiving inputs and displaying outputs for the user 103 to learn, maintain, or improve skills associated with music or musical instruments such as playing a piano. User interface 114 may include guidance indicators 208 as discussed above, augmented portions 302*a-d* including an augmented reality image of a desired reaction for user 103 such as finger outlines guiding the user 103 to figure placements for a particular musical piece), an environment portion 306 including a real-time environment (e.g., user 103 playing a piano), guidance indicators 308*a-d* indicating a level of speed, distance, direction, or force for the user 103 to move or apply, and first and second body portions 322*a*, 322*b* of user 103. User 114 may provide updated guidance objects with an updated speed, distance, direction, or force in response to a user reaction of user 103 or inputs from user 101, e.g., sounds of actual playing of piano by user.

As an example, user interface 114 may display augmented portions 302*a-d*, e.g., finger or hand placements of a skilled pianist on a keyboard of a piano following the strokes of the pianist for a particular musical piece as part of the guidance information). The user interface 114 may display the guidance information at a lower or first speed for a predefined or user-defined time as part of the guidance information, and then speed the guidance information up to a higher or second speed in response to the reactions of the user 103, e.g., as the skills of user 103 improve.

FIG. 4 illustrates display screen 400 with user interface 114 configured to display guidance objects, e.g., for a user 103 to learn, maintain, or improve skills associated with physical activities or sports such as tennis. User interface 114 may include guidance indicators 208 as discussed above, augmented portions 402*a-c* including an augmented reality image of a desired reaction for user 103 such as object placement 402*a* and limb placements 402*b*, 403*c* so as to hold guidance object 410 such as a racket (e.g., tennis racket) so as to hit or connect with guidance object 412 such as a ball (e.g., tennis ball), a guidance window 404 with user 101 such as an instructor (e.g., tennis instructor) providing guidance to user 103 including desired limb placements 424*a*, 424*b* and desired object placement 426, an environment portion 406 including a real-time environment of user 103 (e.g., user 103 playing tennis), an environment portion 306 including a real-time environment (e.g., user 103 playing a piano), and first and second body portions 422*a*, 422*b* of user 103. User interface 114 may provide updated guidance objects with an updated speed, distance, and direction in response to a user reaction of user 103 or inputs from user 101.

User interface 114 may display guidance objects associated with learning, maintaining, or improving physical and mental skills including fine and coarse psychomotor skills, e.g., for physical activities, art, sports, and physical rehabilitation. For example, user interface 114 may be configured to display guidance objects including and for learning martial arts such as tai chi by user 103 following motions of an avatar in front of the user 103. The avatar may be facing toward user 103 or in the same direction as user 103. The limbs of the avatar may be superimposed or overlaid on the limbs of the user 103.

Examples may include, by way of user interface 114, guidance objects allowing user 103 to practice motor skills by following motions of a skilled person in the area of art or sports that user 103 is practicing. User interface 114 may cause user 103 to follow the motions of the skilled person that is superimposed or overlaid on the body or limb of user 103. For example, user 104 may be in a real-time environment of sitting at a piano and the guidance objects may include fingers of an avatar, a marker on the keys they have to press for a musical piece, or other guidance objects that encouraging the user 103 to follow. The guidance objects start a first speed or pace for a predefined or user-defined time period and then increase to a second speed or pace over time or after a second predefined or user-defined time period. The guidance object may include an augmented image of a paintbrush, encouraging user 103 to follow its motions so as to paint a picture. The guidance object may include a trainer such as a martial arts or dance trainer, which may be in a user-defined orientation such as in front of user 103 so that user 103 may follow the motion of the trainer. Again, user interface 114 may be configured to allow user 103 to define the pace and speed of the motion of the trainer as well as pause, rewind, and replay the trainer motions. This can also be used learning dancing with an augmented reality image of a dance partner, or practicing ping pong with an augmented reality image of an avatar. As such, the augmented reality image may be displayed as overlaid on the body parts or in the field of view of the user.

Figure 5:
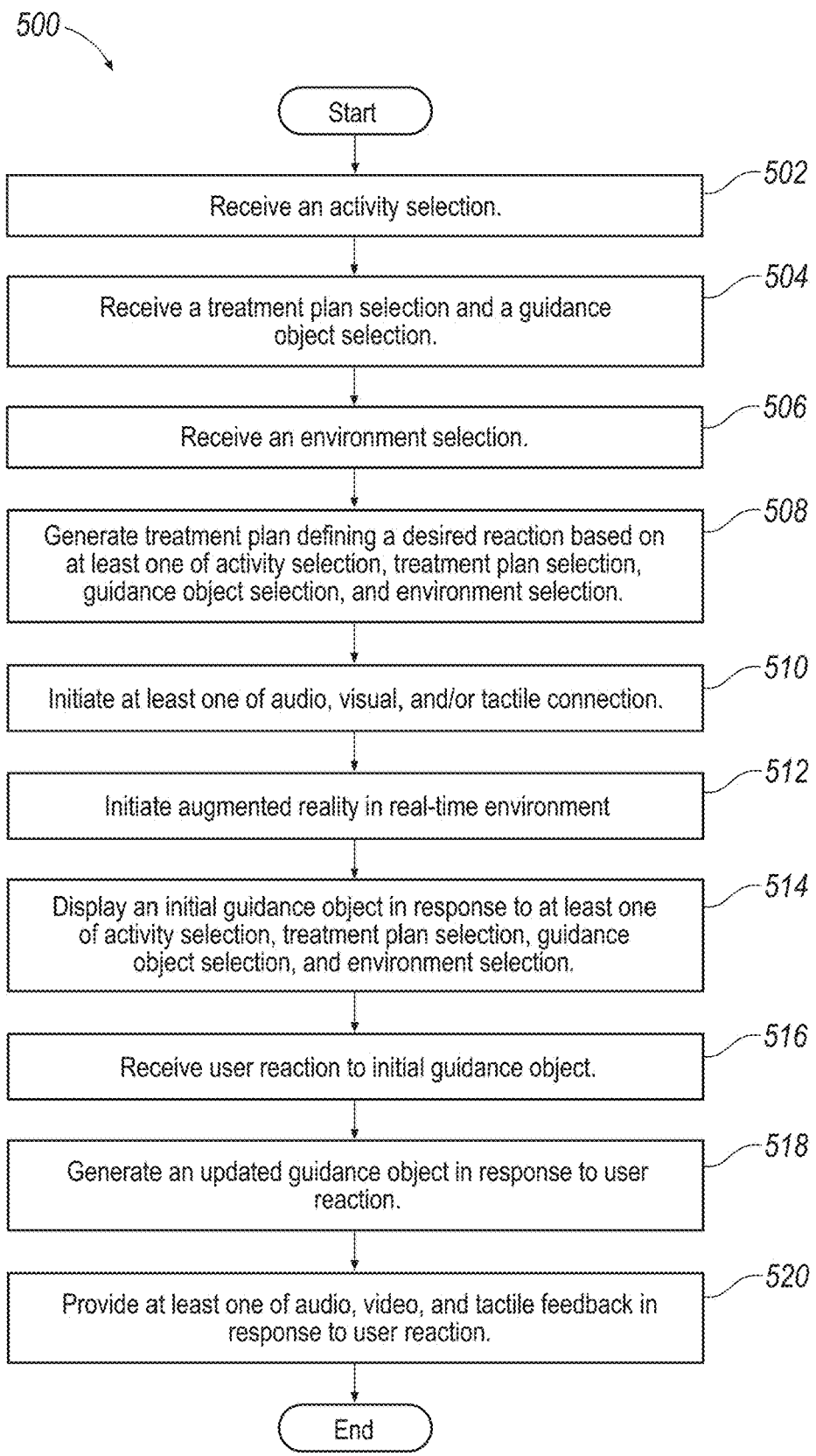
FIG. 5 illustrates an exemplary method of the present disclosure.

FIG. 5 illustrates an exemplary process 500 that may use device 102, device 104, server 105, sensors 116, feedback device 118, network 120, database 122, or a combination thereof, e.g., for user reaction conditioning. Process 500 may take many different forms and include multiple and/or alternate components and facilities. While an exemplary process 500 is shown in FIG. 5, the exemplary steps and components illustrated in FIG. 5 are not intended to be limiting, may be optional, and are not essential to any other step or component. Indeed, additional or alternative components and/or implementations may be used.

At block 502, device 102 or 104 may receive by way of the user interface 114 user, and store by way of memory 108 or database 122, guidance information including an activity selection, e.g., an in-person or remote treatment by user 101 for user 103.

At block 504, device 102 or 104 may receive by way of the user interface 114 user, and store by way of memory 108 or database 122, guidance information including a treatment plan selection and a guidance object selection.

At block 506, device 102 or 104 may receive by way of the user interface 114 user, and store by way of memory 108 or database 122, guidance information including an environment selection.

At block 508, the processor 106 of device 102 or 104, or server 105 in communication with device 102 or 104 by way of network 120, may generate guidance information including a treatment plan defining a desired reaction based on at least one of activity selection, treatment plan selection, guidance object selection, and environment selection.

At block 510, the processor 106 of device 102 or 104 may initiate at least one of audio, visual, and/or tactile connection with the other of the device 102 or 104.

At block 512, the processor 106 of device 102 or 104 may initiate augmented reality in real-time environment as discussed above by way of an augmented reality device such as device 102c or 104a.

At block 514, device 102 or 104 may display by way of user interface 114, and store by way of memory 108 or database 122, an initial guidance object in response to at least one of the activity selection, treatment plan selection, guidance object selection, and environment selection.

At block 516, device 102 or 104 may receive by way of transceiver 112, and store by way of memory 108 or database 122, a user reaction to initial guidance object.

At block 518, processor 106 of device 102 or 104, or server 105 in communication with device 102 or 104 by way of network 120, may generate, and store by way of memory 108 or database 122, an updated guidance object in response to user reaction.

At block 520, device 102 or 104 may provide by way of a feedback device at least one of audio, video, and tactile feedback in response to user reaction. After block 520, the process 500 ends.

Figure 6:
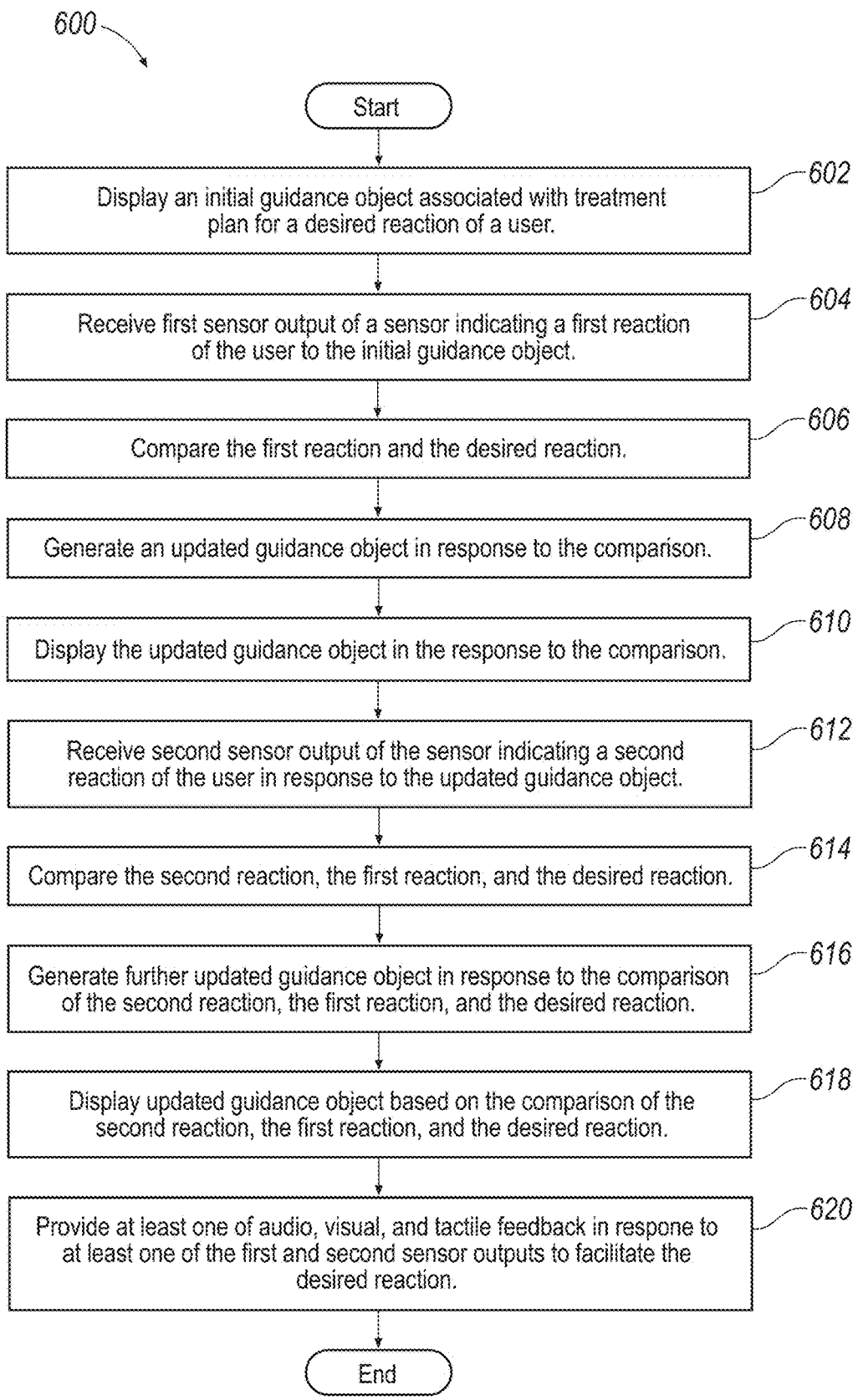
FIG. 6 illustrates another exemplary method of the present disclosure.

FIG. 6 illustrates an exemplary process 600 that may use device 102, device 104, server 105, sensors 116, feedback device 118, network 120, database 122, or a combination thereof, e.g., for user reaction conditioning. Process 600 may take many different forms and include multiple and/or alternate components and facilities. While an exemplary process 600 is shown in FIG. 6, the exemplary steps and components illustrated in FIG. 6 are not intended to be limiting, may be optional, and are not essential to any other step or component. Indeed, additional or alternative components and/or implementations may be used. For instance, process 600 may be implemented numerous times to continually update and display guidance or feedback to the user during one or more treatment sessions.

At block 602, device 102 or 104 may display by way of the user interface 114, and store as guidance information by way of memory 108 or database 122, an initial guidance object associated with a treatment plan for a desired reaction of the user 103, e.g., defined as part of guidance information by the user 101 using the user interface 114 of device 102.

At block 604, device 102 or 104 may receive by way of the transceiver 112, and store as guidance information by way of memory 108 or database 122, a first sensor output of the sensor 116 indicating a first reaction of the user 103 to the initial guidance object.

At block 606, the processor 106 of device 102 or 104, or server 105 in communication with device 102 or 104 by way of network 120, compare the first reaction of user 103 and the desired reaction of the treatment plan.

At block 608, the processor 106 of device 102 or 104, or server 105 in communication with device 102 or 104 by way of network 120, may generate, and store as guidance information by way of memory 108 or database 122, an updated guidance object in response to the comparison of the first reaction and the desired reaction.

At block 610, device 102 or 104 may display by way of the user interface 114 the updated guidance object based on the comparison of the first reaction and the desired reaction.

At block 612, the processor 106 of device 102 or 104 may receive by way of the transceiver 112, and store as guidance information by way of memory 108 or database 122, a second sensor output of the sensor 116 indicating a second reaction of the user 103 in response to the updated guidance object.

At block 614, the processor 106 of device 102 or 104, or server 105 in communication with device 102 or 104 by way of network 120, may compare the second reaction, the first reaction, and the desired reaction.

At block 616, the processor 106 of device 102 or 104, or server 105 in communication with device 102 or 104, may generate, and store as guidance information by way of memory 108 or database 122, a further updated guidance object in response to the comparison of the second reaction, the first reaction, and the desired reaction.

At block 618, device 102 or 104 may display by way of the user interface 114 the updated guidance object based on the comparison of the second reaction, the first reaction, and the desired reaction.

At block 620, device 102 or 104 may provide by way of a feedback device at least one of audio, visual, and tactile feedback in response to at least one of the first and second sensor outputs to facilitate the desired reaction. After block 620, the process 600 ends.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain examples, and should in no way be construed so as to limit the claims.

Accordingly, it is to be understood that the above description is intended to be illustrative and not restrictive. Many examples and applications other than those provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future examples. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus the following claims are hereby incorporated into the Detailed Description, with each claim standing on its own as a separately claimed subject matter.

What is claimed is:

1. A system comprising:
   an augmented reality device having a user interface to display an augmented reality image such that the augmented reality image appears on an environmental region of an actual environment;
   a transceiver that communicatively connects a guidance window of the user interface of the augmented reality device to a practitioner device;
   a hardware processor and a memory having a program communicatively connected to the hardware processor, the hardware processor being communicatively connected to a user body sensor and a user feedback device, the hardware processor providing operations including:
   display, by way of the user interface, an initial guidance object associated with a desired reaction of a user; and
   provide, by way of the user interface and user feedback device, real-time guidance from the practitioner device including an updated guidance object based on the user body sensor and a comparison of a first reaction of the user and the desired reaction according to the practitioner device.

2. The system of claim 1,
   the operations of the hardware processor further including:
   receive, by way of the transceiver, a first sensor output including a field of view according to the user body sensor and indicating the first reaction of the user to the initial guidance object;
   the comparison including compare, by way of the hardware processor, the first reaction and the desired reaction; and
   generate, by way of the hardware processor, the updated guidance object in response to the comparison of the first reaction and the desired reaction.

3. The system of claim 1, wherein the desired reaction of the user includes a desired limb placement, and the operations of the hardware processor further including:
   provide, by way of the user interface, a transparent area and an augmented area, wherein the transparent area allows the user to view the actual environment of the user and the augmented area displays the augmented reality image relative to the actual environment, wherein the augmented reality image includes at least one of the initial and the updated guidance objects in response to the comparison by the hardware processor of the first reaction of the user and the desired limb placement.

4. The system of claim 1, the operations of the hardware processor further including:
   initiate, by way of the transceiver, at least one of a video, audio, and tactile connection with the practitioner device.

5. The system of claim 1, the operations of the hardware processor further including at least one of:
   receive, by way of the transceiver, at least one of the initial and updated guidance objects in response to a practitioner selection by the practitioner device of at least one of an activity selection, a treatment plan selection, a guidance object selection, and an environment selection; or
   generate, by way of the hardware processor, at least one of the initial and updated guidance objects in response to a user selection by the user interface of at least one of the activity selection, the treatment plan selection, the guidance object selection, and the environment selection.

6. The system of claim 3, the operations of the hardware processor further including:
   receive, by way of the transceiver, a second sensor output of the user body sensor indicating a second reaction of the user in response to the updated guidance object; and compare, by way of the hardware processor, the second reaction, the first reaction, and the desired reaction.

7. The system of claim 3, the operations of the hardware processor further including:
generate, by way of the hardware processor, a further updated guidance object in response to the comparison of a second reaction, the first reaction, and the desired reaction; and
display, by way of the user interface, the updated guidance object based on the comparison of the second reaction, the first reaction, and the desired reaction.

8. The system of claim 3, the operations of the hardware processor further including:
provide, by way of the feedback device in communication with the augmented reality device, at least one of audio, visual, and tactile feedback in response to at least one of the first and second sensor outputs to facilitate the desired reaction; and
display, by way of the user interface of the augmented reality device, the guidance object with an updated speed, distance and direction in response to at least one of the first and second reactions of the user.

9. A non-transitory computer-readable medium tangibly embodying computer-executable instructions of a program being executable by a hardware processor of a computing device with a user interface to provide operations comprising:
provide an augmented reality device in communication with a practitioner device, and having a user feedback device and a user interface to display an augmented reality image such that the augmented reality image appears on an environmental region of an actual environment;
display the augmented reality image including an initial guidance object associated with a desired reaction of a user;
receive a first sensor output of a user body sensor indicating a first reaction of the user to the initial guidance object;
compare the first reaction and the desired reaction;
generate an updated guidance object in response to the comparison of the first reaction and the desired reaction; and
provide, by way of the user interface and the user feedback device, real-time guidance from the practitioner device including the updated guidance object based on the user body sensor and the comparison of the first reaction and the desired reaction according to the practitioner device.

10. The medium of claim 9, wherein the user interface includes an augmented reality device, and the desired reaction of the user includes a desired limb placement, and the operations further comprising:
providing, by way of the user interface, a transparent area and an augmented area, wherein the transparent area allows the user to view the actual environment of the user, the augmented area displays an augmented reality image relative to the actual environment, and the augmented reality image includes at least one of the initial and updated guidance objects in response to the comparison by the hardware processor of the first reaction of the user and the desired limb placement.

11. The medium of claim 9, the operations further comprising:
initiate, by way of a transceiver, at least one of a video, audio, and tactile connection with the practitioner device.

12. The medium of claim 9, the operations further comprising at least one of:
receive, by way of a transceiver, at least one of the initial and updated guidance objects in response to a practitioner selection by the practitioner device of at least one of an activity selection, a treatment plan selection, a guidance object selection, and an environment selection; or
generate, by way of the hardware processor, at least one of the initial and updated guidance objects in response to a user selection by the user interface of at least one of the activity selection, the treatment plan selection, the guidance object selection, and the environment selection.

13. The medium of claim 9, the operations further comprising:
receive, by way of a transceiver, a second sensor output of the user body sensor and indicating a second reaction of the user in response to the updated guidance object; and
compare, by way of the hardware processor, the second reaction, the first reaction, and the desired reaction.

14. The medium of claim 9, the operations further comprising:
generate, by way of the hardware processor, a further updated guidance object in response to the comparison of a second reaction, the first reaction, and the desired reaction; and
display, by way of the user interface, the updated guidance object based on the comparison of the second reaction, the first reaction, and the desired reaction.

15. The medium of claim 9, the operations further comprising:
provide, by way of the user feedback device, at least one of audio, visual, and tactile feedback in response to at least one of the first and second sensor outputs to facilitate the desired reaction; and
display, by way of the user interface of the augmented reality device, the guidance object with an updated speed, distance and direction in response to at least one of the first and second reactions of the user.

16. A method comprising:
providing an augmented reality device in communication with a practitioner device, and having a user feedback device and a user interface to display an augmented reality image such that the augmented reality image appears on an environmental region of an actual environment;
displaying the augmented reality image including an initial guidance object associated with a desired reaction of a user;
receiving a first reaction of the user to the initial guidance object;
comparing the first reaction and the desired reaction;
generating an updated guidance object in response to the comparison of the first reaction and the desired reaction; and
providing, by way of the user interface and the user feedback device, real-time guidance from the practitioner device including the updated guidance object based on the user body sensor and the comparison of the first reaction and the desired reaction according to the practitioner device.

17. The method of claim 16, further comprising:
communicatively connecting, by way of a transceiver, a user interface of an augmented reality device to the practitioner device;

initiating a videoconference with the practitioner device; and displaying, by way of the user interface of the augmented reality device, an augmented reality image and a guidance indictor relative to the augmented reality image in response to the videoconference with the practitioner device.

18. The method of claim 16, further comprising at least one of:

receiving at least one of the initial and updated guidance objects in response to a practitioner selection by the practitioner device of at least one of an activity selection, a treatment plan selection, a guidance object selection, and an environment selection; or generating at least one of the initial and updated guidance objects in response to a user selection by the user interface of at least one of the activity selection, the treatment plan selection, the guidance object selection, and the environment selection.

19. The method of claim 16, further comprising:

receiving a second reaction of the user in response to the updated guidance object; and comparing the second reaction, the first reaction, and the desired reaction.

20. The method of claim 16, further comprising:

generating a further updated guidance object in response to the comparison of a second reaction, the first reaction, and the desired reaction;

presenting the updated guidance object with an updated speed, distance and direction based on the comparison of the second reaction, the first reaction, and the desired reaction; and providing at least one of audio, visual, and tactile feedback to facilitate the desired reaction.

* * * * *